US00RE34421E

United States Patent [19]

Parker et al.

[11] E Patent Number: Re. 34,421

[45] Reissued Date of Patent: Oct. 26, 1993

[54] X-RAY MICRO-TUBE AND METHOD OF USE IN RADIATION ONCOLOGY

[76] Inventors: William J. Parker, 7016 Vicky Ave., West Hills, Calif. 91307; Earl R. Parker, 862 W. Hillsdale Blvd., San Mateo, Calif. 94403

[21] Appl. No.: 870,145

[22] Filed: Apr. 17, 1992

Related U.S. Patent Documents

Reissue of:

[64] Patent No.: 5,090,043
Issued: Feb. 18, 1992
Appl. No.: 616,397
Filed: Nov. 21, 1990

[51] Int. Cl.[5] ..... H01J 35/32

[52] U.S. Cl. ..... 378/121; 378/65; 378/122

[58] Field of Search ..... 378/64, 65, 119, 121–123, 378/130, 140; 600/1–3, 6, 7

[56] References Cited

U.S. PATENT DOCUMENTS

| | | | |
|---|---|---|---|
| 1,881,448 | 10/1932 | Forde et al. | 378/121 |
| 3,714,486 | 1/1973 | McCrary | 313/55 |
| 4,701,941 | 10/1987 | Szirmai et al. | 378/119 |

OTHER PUBLICATIONS

Dunlee OL-1-DL-7, Stationary Anode Isert, Brochures, Jun. 1972.

*Primary Examiner*—David P. Porta

[57] ABSTRACT

An apparatus and method for the treatment of a patient having a tumor is disclosed. An X-ray generating source is positionable at a location in close proximity to the tumor. The X-ray generating source is operable at a voltage level in the range of approximately 10–60 KeV, thereby enhancing absorption of the generated X-rays by the tumor and minimizing the side effects of radiation therapy on the patient's normal tissue.

19 Claims, 4 Drawing Sheets

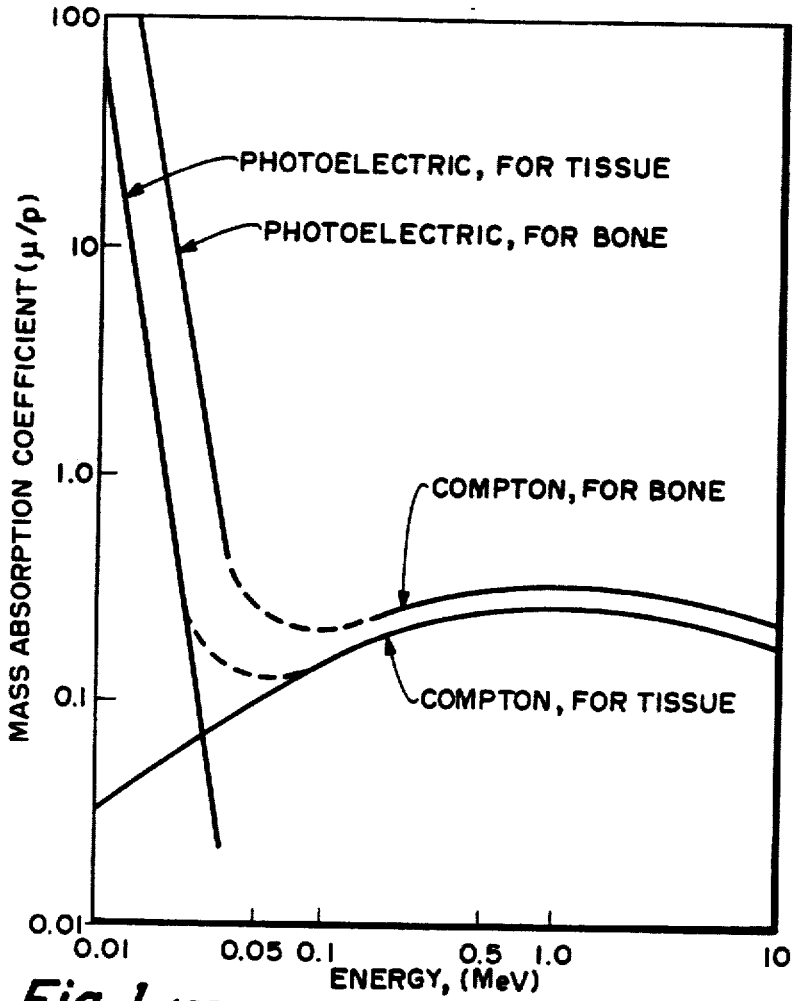
*Fig. 1.* (PRIOR ART) RANGES FOR PHOTOELECTRIC AND COMPTON SCATTERING ABSORPTION.
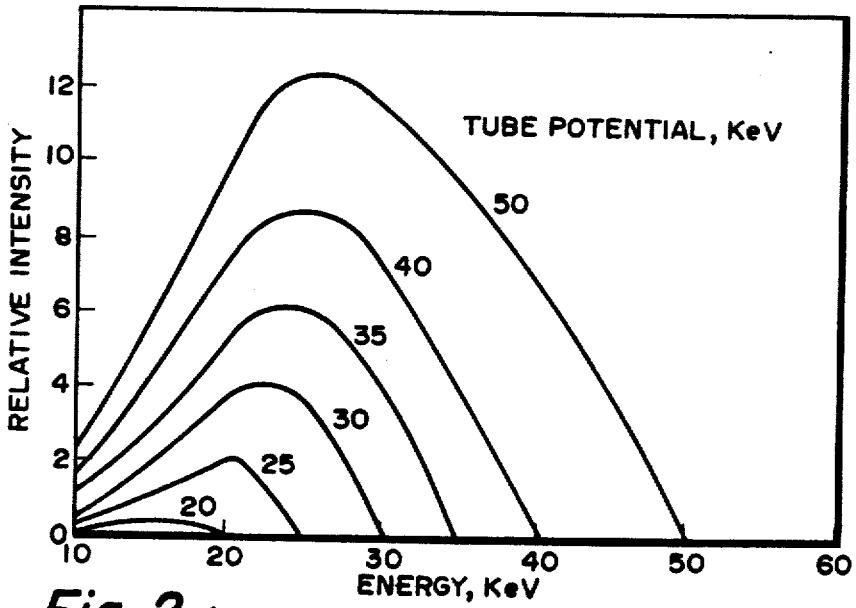
*Fig. 2.* (PRIOR ART) SPECTRAL DISTRIBUTION OF THE X-RAY ENERGIES AND RELATIVE INTENSITIES EMITTED FROM A TUNGSTEN ANODE FOR VARIOUS CONSTANT D.C. POTENTIALS.

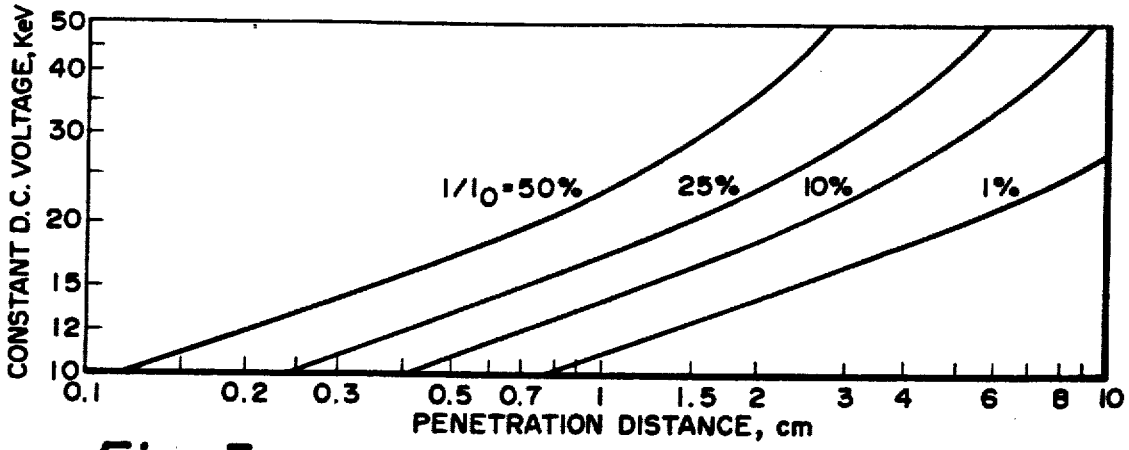
*Fig. 3.* PENETRATION-DEPTH FOR MONOCHROMATIC X-RAYS, ILLUSTRATING DISTANCE FOR PERCENTAGE OF INTENSITY REMAINING.
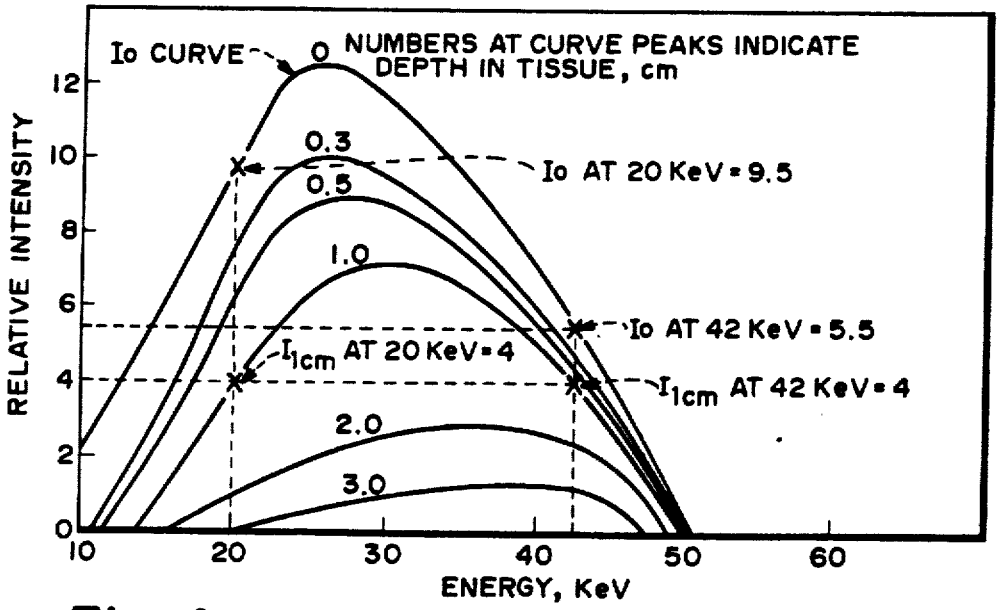
*Fig. 4.* INTENSITY DISTRIBUTIONS OF THE WHITE RADIATION SPECTRUM FROM A TUNGSTEN ANODE AT 50 KeV CONSTANT POTENTIAL D.C. AFTER PENETRATING THROUGH VARIOUS DEPTHS OF TISSUE.
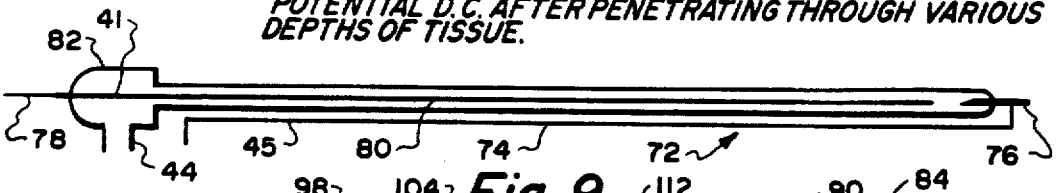
*Fig. 9.*
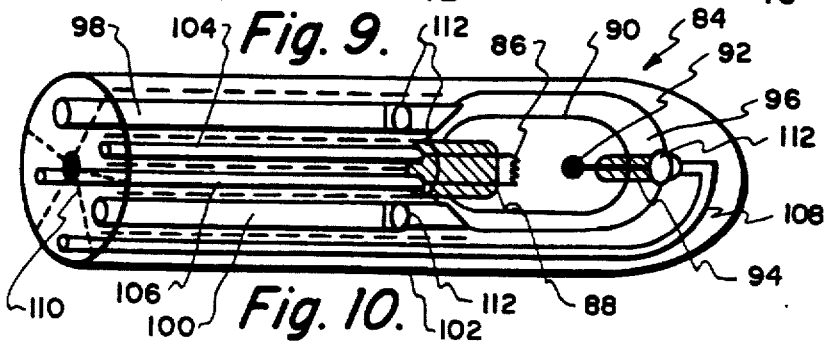
*Fig. 10.*

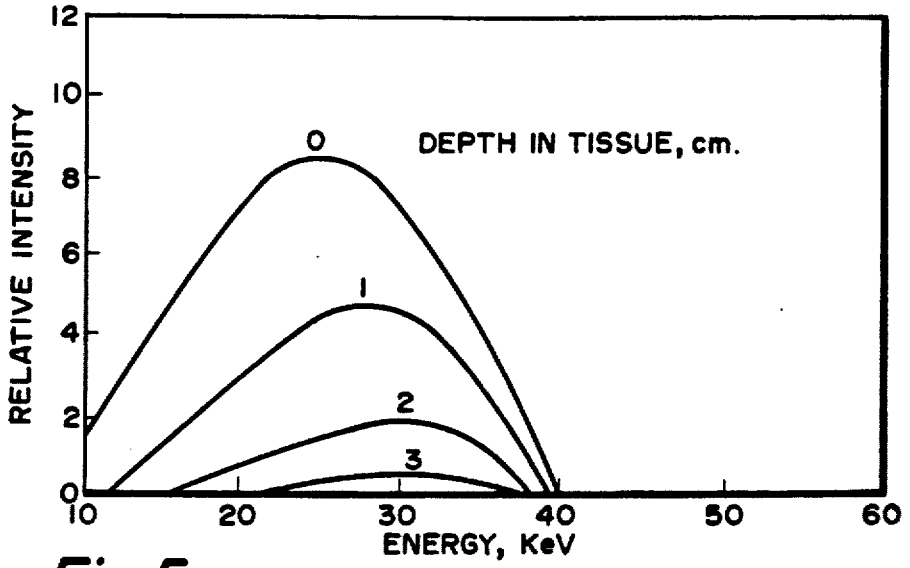
*Fig. 5.* INTENSITY DISTRIBUTION OF THE WHITE RADIATION SPECTRUM FROM A TUNGSTEN ANODE AT 40 KeV CONSTANT POTENTIAL D.C. AFTER PENETRATING THROUGH VARIOUS DEPTHS OF TISSUE.
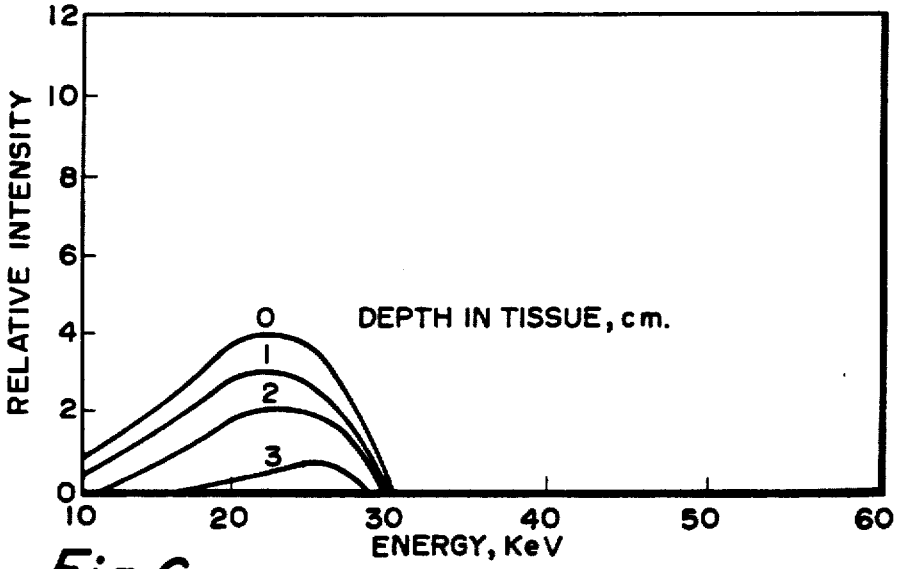
*Fig. 6.* INTENSITY DISTRIBUTION OF THE WHITE RADIATION SPECTRUM FROM A TUNGSTEN ANODE AT 30 KeV CONSTANT POTENTIAL D.C. AFTER PENETRATING THROUGH VARIOUS DEPTHS OF TISSUE.
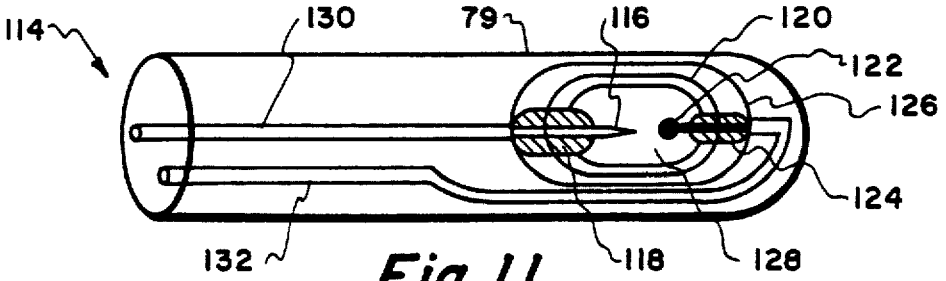
*Fig. 11.*

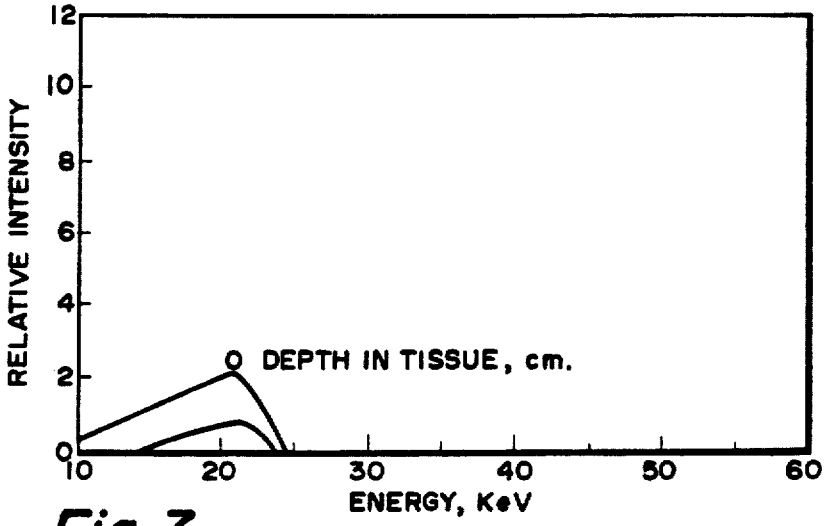
Fig. 7. INTENSITY DISTRIBUTION OF THE WHITE RADIATION SPECTRUM FROM A TUNGSTEN ANODE AT 25 KeV CONSTANT POTENTIAL D.C. AFTER PENETRATING THROUGH VARIOUS DEPTHS OF TISSUE.
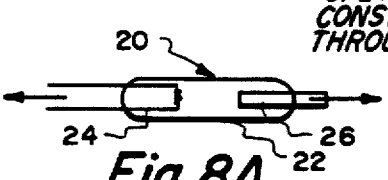
Fig. 8A.
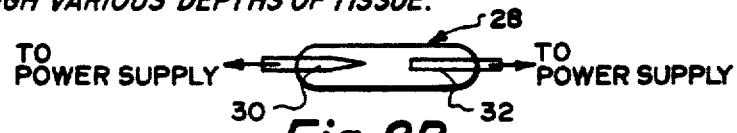
Fig. 8B.
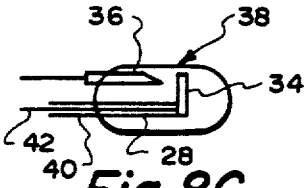
Fig. 8C.
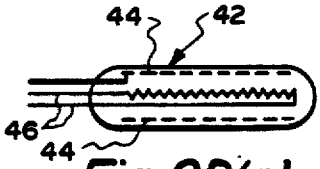
Fig. 8D(a).
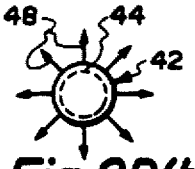
Fig. 8D(b).
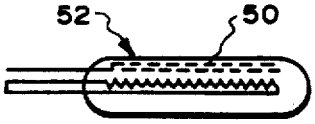
Fig. 8E(a)
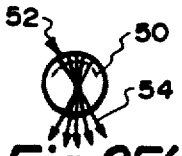
Fig. 8E(b).
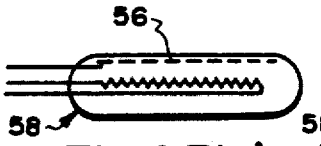
Fig. 8F(a).
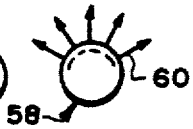
Fig. 8F(b).
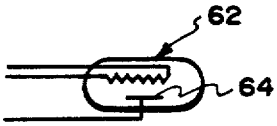
Fig. 8G.
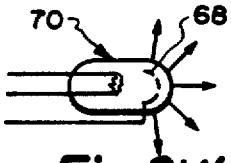
Fig. 8H(a).
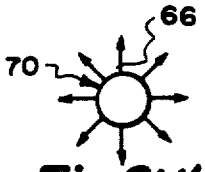
Fig. 8H(b).

X-RAY MICRO-TUBE AND METHOD OF USE IN RADIATION ONCOLOGY

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to the production and medical use of X-rays, and more particularly to the production, by X-ray micro-tubes, of low energy, highly absorable, polychromatic X-rays and to the use of those X-rays in the treatment of tumors when such X-rays micro-tubes are placed within, or adjacent to, mammalian bodies in very close proximity to, or within, tumors.

2. Description of Related Art

Its has been stated that the goal of radiation therapy is to achieve in a selected treatment volume, a dose distribution of radiation that provides the patient with maximum tumor control and the least possible effect on surrounding normal tissues. (PRINCIPLES AND PRACTICE OF RADIATION ONCOLOGY, C. A. Perez, and L. W. Brady, Editors; J. B. Lippincott Company, Philadelphia. 1987 Pg. 159).

To achieve that desired goal, many methods have been advanced over the last 90 or so years which have focused on the use of very high energy sources of radiation. Current radiation treatment of tumors involves the use of large external high energy devices such as X-ray machines, linear accelerators, betatrons, or microtrons, or the use of very high energy emissions from radiosotopes.

the radioisotopes may be placed in large external machines such as $^{60}$Cobalt teletherapy machine, or implanted near a tumor site. Present Applicants are aware of a surgical procedure being utilized in the treatment of brain tumors in which tiny holes are drilled in the skull. The surgeon inserts thin tubes with closed bottom ends into the tumor. Radioactive pellets the size of peas are inserted into the tubes. The implants deliver strong radiation to the tumor. They are removed few days later.

The safety of these above-identified high energy radiation sources has been a constant concern for health professionals. Not only can the tumor and surrounding normal tissue within the patient be affected by these high energy radiation sources, but the health professionals working near the patient can be adversely affected if adequate safeguards are not taken.

Although the high energy devices have been designed to produce a maximum of antitumor activity with a minimal effect on a patient's normal tissues, the side effects of the radiation therapy on the patient's normal tissue can still be the limiting factor in a course of therapy.

SUMMARY OF THE INVENTION

The present invention is a method and apparatus for treating tumors by low energy, highly absorbable, polychromatic X-rays (also called Bremsstrahlung or White radiation) produced by small X-ray micro-tubes placed within, or adjacent to, a patient's body in close proximity to, or within, a tumor. The design of the X-ray micro-tube can be relatively simple: a miniature X-ray production source, generally a glass tube a fraction of an inch in diameter and with a length of approximately one-half of an inch, to several inches, containing at least an anode and a cathode. The cathode may be a pointed cold cathode, or a heated filament, and the tube must be evacuated to, at most, $10^{-6}$ Torr. The target portion of the anode may be formed of tungsten, as in conventional X-ray tubes. The glass tube may be surrounded by a plastic envelope so as to prevent injury to the patient or health professional should the glass break. A metal jacket containing a window may be placed around the tube so as to allow the X-rays to travel only in the direction of the tumor. The X-ray micro-tube may be disposable or re-sterilized.

The depth of X-ray penetration into tissues can be easily and accurately controlled by adjusting the voltage applied to the X-ray micro-tube. Tissue penetration depths within a few centimeters from the surface of the tube are characteristic of the White radiation produced by the micro-tubes. This reduces damage to normal tissue except in the immediate vicinity of the tumor. The X-rays are produced by applied voltages between 10 kilovolts and 60 kilovolts.

The voltage applied to the X-ray micro-tube may have an operable frequency between direct current and 1,000,000 cycles per second, the higher frequencies providing greater patient safety. The current through the X-ray micro-tube is generally much lower than that conventionally used and is in the micro-ampere range. Patient safety is assured by ground fault interrupters and current limiting circuitry.

The micro-X-ray tubes may be place in-situ by a number of methods, including, but not limited to: implantation during surgery; insertion through a normal body orifice; insertion in conjunction with a fiber-optic scope through a normal body orifice; in conjunction with a fiber-optic scope through a surgical incision; insertion through a trocar catheter; or insertion through a catheter contained within a surgical incision.

Other objects advantages and novel features of the present invention will become apparent from the following detailed description of the invention when considered in conjunction with the accompanying drawings.

BRIEF DESCRIPTION OF THE DRAWINGS

FIG. 1 is a graph of Mass Absorption Coefficient, $\mu/\rho$, versus Energy, MeV, showing the ranges for Photoelectric and Compton Scattering absorption.

FIG. 2 is a graph illustrating the spectral distribution of the X-ray energies and relative intensities emitted from a tungsten anode for various constant d.c. potentials.

FIG. 3 is a graph illustrating examples of Penetration-depth curves of constant d.c. voltage, KeV vs penetration depth in body tissue, in centimeters, for monochromatic X-rays, showing distance for percentage of intensity remaining.

FIG. 4 includes schematic curves showing the changes in the intensity distribution of the White radiation spectrum from a tungsten anode at 50 KeV constant potential d.c. after penetrating through various depths of tissue.

FIG. 5 includes schematic curves showing the changes in the intensity distribution of the White radiation spectrum from a tungsten anode at 40 KeV constant potential d.c. after penetrating through various depths of tissue.

FIG. 6 includes schematic curves showing the changes in the intensity distribution of the White radiation spectrum from a tungsten anode at 30 KeV constant potential d.c. after penetrating through various depths of tissue.

FIG. 7 includes schematic curves showing the changes in the intensity distribution of the White radiation spectrum from a tungsten anode at 25 KeV constant potential d.c. after penetrating through various depths of tissue.

FIGS. 8A to 8J illustrate short X-ray micro-tube designs.

FIG. 8A illustrates a short micro-tube with a heated filament cathode.

FIG. 8B illustrates a short micro-tube with a cold cathode electron emitter.

FIG. 8C illustrates a very short micro-tube having the cathode and anode positioned on the same end, with an internal glass tube for insulating the anode connecting wire.

FIGS. 8D(a) and 8D(b) illustrate the use of a thin internal anode film on the inside of the glass tube through which X-rays can penetrate to produce a cylindrical transmitted X-ray beam.

FIGS. 8E(a) and 8E(b) illustrate the use of a thick internal anode film on the inside of the glass tube, the resulting back-scattered X-ray beam producing a hemicylindrical X-ray pattern.

FIGS. 8F(a) and 8F(b) illustrate the use of a thin internal anode film on the inside of the glass tube resulting in a hemicylindrical transmitted X-ray pattern.

FIG. 8G illustrates a short micro-tube with a spot-type anode (thick or thin).

FIGS. 8H(a) and 8H(b) illustrate the use of a thin internal hemispherical anode film used to produce a hemispherical X-ray pattern.

FIG. 9 illustrates a long micro-tube design with an enlarged end for evacuation and sealing.

FIG. 10 is a schematic illustration of a short liquid-cooled microtube assembly.

FIG. 11 is a schematic illustration of a short metal-jacketed microtube assembly.

The same elements or parts throughout the figures of the drawings are designated by the same reference characters.

DETAILED DESCRIPTION OF THE INVENTION

An understanding of X-ray interaction with tumors requires some background understanding of the physical phenomena involved. Electromagnetic radiation extends over a very wide range of wave lengths, i.e. from radio waves ($3\times10^4$ m to 5 m), microwaves ($5\times10^{-2}$ m to $1\times10^{-4}$ m), infrared ($1\times10^{-4}$ m $7\times10^{-7}$ m), visible ($7\times10^{-7}$ m to $4\times10^{-7}$ m), ultra-violet ($4\times10^{-7}$ m to $1\times10^{-8}$ m), X-rays and gamma rays ($1\times10^{-8}$ m to $1\times10^{-14}$ m). The wave lengths of X-rays are frequently expressed in angstroms (Å) with 1 Å being equal to $10^{-8}$ cm. These selected wave length bands of radiation have been classified as ranges which interact with matter in familiar ways. The value of the wavelength determines the size of an object with which the electromagnetic radiation will react. Radio waves will react with large electrical conductors, visible and ultra-violet light react with the outer shell electrons in atoms, and X-rays interact with the innermost orbital electrons. The shorter the wavelength the higher the energy of the radiation. The reciprocal of the wavelength is the frequency, with the wavelength commonly being represented by the symbol $\lambda$, and the frequency by the Greek letter $\nu$. The energy, E, is equal to $\eta\nu$, where $\eta$ is Planck's constant.

The nature and properties of the radiation within the X-ray band vary with the energy (or wavelength) of the X-ray, just as the characteristics of the light in the visible range vary with the wave length of the radiation, the shorter wave lengths appearing as blue colors and the longer ones as orange-red colors. A brief discussion of how the different wave lengths of X-rays are produced and how they differ in their interactions with body tissues provides an understanding of the uniqueness and value of the present invention.

Medically useful X-rays are normally produced in evacuated tubes (usually made of glass) containing two elements, a cathode and an anode. The cathode is typically a tungsten filament that is heated to a temperature sufficiently high to cause electrons to reach velocities permitting them to escape from the filament. The escaping electrons are attracted to the anode at the opposite end of the tube (also typically formed of tungsten), which exists at a high positive potential, commonly in the range of 50,000 to 2 million volts.

The electrons are accelerated during their passage toward the anode, reaching a high velocity before colliding with the anode and causing inner shell electrons to be ejected from the tungsten atoms. When the high energy ejected to be ejected electrons return to normal positions in electron shells, X-rays are created. The energy gained by the participating electrons is measured in electron volts (eV) where e is the electrical charge of the electron and V is the voltage difference between the cathode and the anode. This measurement of energy is commonly used in the field of X-ray diagnosis and therapy. (For the purpose of comparison, one electron volt of energy per atom is equivalent to 23 kilocalories per mole of atoms).

In the X-ray range of wave lengths, several different phenomena occur when matter is exposed to X-rays. These phenomena are known as Elastic (or Coherent) Scattering, Photoelectric Absorption, Compton Scatter, and Electron Pair Production (one electron and one position). When the energy of the photon is less than the binding energy of the outer shell electrons of the exposed material, the photons cause the orbiting electrons to oscillate in phase with the X-ray and thus to emit electromagnetic radiation of the same frequency as the incident ray. The re-radiated X-rays are scattered with no absorption in the irradiated matter. This phenomenon, called Elastic or Coherent Scattering, is of no consequence in X-ray diagnosis or therapy. Electron Pair Production only occurs at extremely high energies i.e., above one million electron volts (1 MeV), which is much higher than the energies used in this invention. Thus, these two phenomena will not be further discussed herein.

Photoelectric Absorption is the dominant form of X-ray absorption only in the lowest range of X-rays (e.g. 10 to 60 kilovolts). It occurs when the energy of the X-ray photons is equal to the energy binding the innermost shell electrons of the atoms in the exposed matter. In this case, the X-ray photons interact with the electrons orbiting closest to the nucleus, causing them to be ejected from the atoms, and causing the photons to loose all of their energy and disappear. This reaction cannot occur at X-ray beam energies below the electron-atom binding energy. It is a maximum when the two energies are equal, and decreases rapidly with increasing X-ray energy above the maximum value.

Absorption of higher energy X-ray radiation (e.g. above 100 KeV) occurs almost entirely by Compton Scattering. This process involves the interactions of X-ray photons with any of the electrons in the cloud surrounding the nucleus of the interacting atom. In this case, an incident photon loses only part of its energy when it reacts with an electron, which acquires the energy lost by the photon and is ejected from the electron cloud of the atom. The resulting photon with diminished energy is scattered and moves forward at some angle to the line of the incident beam. The energy of the scattered photon is not absorbed locally within the exposed material during this event, but the energy acquired by the participating electron is completely absorbed within the material. Thus, the energy change of the incident X-ray beam is divided into two parts, only one of which is directly absorbed.

Between 10 KeV and 100 KeV the absorbed fraction of Compton energy increases from a low value at 10 KeV, finally reaching a high value at 100 KeV, thereafter changing by a relatively small amount in the range between 100 KeV and 1 MeV as shown on the mass absorption coefficient vs energy curves in FIG. 1. (FIG. 1 is prior art adapted from "Principles of Radiological Physics" by Robin J. Wilkes. Second Edition, Pg. 483. Churchill Livingstone, N.Y. 1987.) In this figure there are curves showing how the absorption of X-rays by tissue and bone vary with photon energy. Below about 50 KeV energy (in the Photoelectric Absorption range), bones absorb about 13 times as much of the incident energy as does tissue. Above about 100 KeV (in the Compton range) the difference is very small, with bone absorption being only about 1.7 times as much as tissue. The higher energy range is generally used for cancer therapy.

The photoelectric absorption of 10 KeV X-rays by tissue is very high, but the absorption coefficient decreases drastically as the energy is increased. At 50 KeV the absorption coefficient has decreased to about one percent of the 10 KeV value. In the 10 KeV to 50 KeV range in which Photoelectric Absorption is dominant. These lower energy X-rays penetrate only short distances into tissue and consequently this is not normally considered to be useful range for either medical diagnosis or therapy. It is common practice in radiation therapy to remove as much as possible of this skin damaging radiation from the X-ray beam. This is accomplished by inserting thin sheets of aluminum or copper in the path of the beam to absorb as much as possible of the low energy component of the beam. The present invention makes it possible to utilize some of the X-rays in this low energy range to treat some easily accessible cancerous tissue more effectively than the higher energy methods now in use, but without the sometimes severe damage to normal body tissue that occurs with currently used practices.

Before entering into the detailed description of the new method and equipment which are the subject of this invention, a brief description of some of the well known characteristics and methods of utilizing X-rays is considered. For example, traditional plots of absorption coefficients versus X-ray energies, such as illustrated in FIG. 1, refer to monochromatic X-rays, whereas the radiation from an X-ray tube actually comprises a broad spectrum of energies, as illustrated by FIG. 2. (FIG. 2 is prior art adapted from "X-Ray Metallography" by A. Taylor, pg. 18, John Wiley and Sons, New York, 1961)

In this figure relative (X-ray) intensity is plotted against (X-ray) energy for various constant d.c. tube voltages, and spectral curves of Bremsstrahlung or White radiation are thus produced. The shapes of these curves are affected by tube potential. The shapes of the curves are also affected by the nature of the power source. Depending upon the design of the power supply, the output may be constant d.c., a half-wave rectified a.c., or a full wave rectified a.c.. The maximum intensities and the X-ray energy distribution will be different for each type of power source. Also, it must be remembered that the mass absorption coefficient for tissue varies sharply with the energy (or wave length) of the X-ray, as shown in FIG. 1. In reality, then, the effective absorption coefficient for a beam consisting of a broad spectrum of X-rays is the fraction of the beam that is absorbed during the passage of the beam through one centimeter of material and is composed of two parts: one being the component contributed by Photoelectric Absorption, and the other being due to the Compton effect.

FIG. 3 shows examples of approximate depth of penetration curves (i.e. the distance through material which causes a specific decrease in the X-ray intensity to, for example, ½, ¼, 1/10 etc. of the initial beam intensity. I is the intensity, while $I_o$ refers to the initial intensity). The values shown in this figure are for monochromatic radiation. From accurate plots of the mass absorption coefficients, $\mu/\rho$, versus energy curves shown in FIG. 1, the linear absorption coefficient, $\mu$, needed for calculating the decrease in X-ray intensity versus penetration distance, as shown in FIG. 3, can be obtained by assuming that the intensity, $\rho$, of tissue used for defining mass absorption coefficient, $\mu/\rho$, is equal to 1. FIG. 3 highlights the fact that in the 10–50 KeV range X-rays simply do not penetrate very far.

As an example of the method used to obtain the curves in FIG. 3, assuming the voltage to be 50 KeV, the value of $I/I_o=0.5$, and $\mu$, the absorption coefficient $=0.24$, the interrelationship of these parameters is given by $I/I_o=e^{-\mu x}$ where x is the penetration distance below the surface of the absorbing material (x is a negative number). Substituting the numbers given above in the equation yields a value of x of 2.87 cm (corresponding to the value for the $x=2.87$ cm at 50 KeV and 50% absorption in FIG. 3).

The actual radiation being emitted from the anode on an X-ray tube with, for example, 50 kilovolts applied potential, is actually a whole spectrum of radiant energies, producing what is commonly called "white" radiation. This is illustrated in FIG. 2, which shows the distribution of energies (in KeV) for a tube with a tungsten anode, when exposed to various constant tube voltages. In spectra of this sort, each individual value would have an absorption coefficient differing from those of the other energies in the spectrum. The variation in absorption coefficients within the spectrum must be taken into account when effective absorption is calculated for the beam. In the lower end of the voltage range, i.e., below about 50 KeV tube voltage, the absorption coefficients may vary by more than 100 to 1 (see FIG. 1). However, in the higher voltage range currently in general use (i.e., about 100 KeV to 1 MeV) the absorption coefficient is relatively constant. With white radiation in the energy range of this invention, then, both the absorption coefficient and the X-ray intensity are strongly dependent upon the energy of the photons involved. For example, the mass absorption coefficient for tissue varies from about 0.33 for 37 KeV to 3.3 at 12 KeV.

FIGS. 4, 5, 6, and 7 show intensity decreases in the initial intensity values for white radiation from a tungsten anode X-ray tube at different tube potentials, as the beam penetrates into tissue. The shape of the Relative Intensity versus Energy (KeV) curve changes as the distance from the outer surface of the tissue being penetrated is increased. At each X-ray energy level the absorption coefficient differs, as shown in FIG. 1, with a much higher fraction of the lower X-ray energy components of the white radiation beam being absorbed than is the case for the higher energy components. The curves in FIG. 4 illustrate this effect at various depths in tissue.

Examples of how and why the shapes of the white radiation energy distribution curves change at different depths in tissue will be helpful in understanding the curves plotted in FIGS. 4, 5, 6, and 7. FIG. 4 illustrates examples of the nature of the changes that occur at a high energy value within the 50 KeV generated white radiation spectrum, to those of a low energy value of the same spectrum, by comparing initial intensities on the $I_o$ curve to intensities on the same depth in tissue curve.

In this example, let the high energy case by chosen as 42 KeV and the low energy be selected as 20 KeV. For the high energy case (42 KeV), let: $I_o=5.5$ (from FIG. 4), $\mu=0.32$ (from FIG. 1), and $x=1$ cm.

By rearranging the formula, $I/I_o=e^{-\mu x}$, we can solve for the value of I at 1 cm using our parameters:

$$I_{Icm}=I_O e^{-\mu x}$$

$$I_{Icm}=5.5e^{-(0.32)(1)}$$

$$I_{Icm}=5.5/1.38$$

$$I_{Icm}=4,$$

which is shown on FIG. 4.

Now, for the low energy case (20 KeV), let: $I_o=9.5$ (from FIG. 4), $\mu=0.87$ (from FIG. 1), and $x=1$ cm.

In this case, we have:

$$I_{Icm}=9.5e^{-0.87}$$

$$I_{Icm}=9.5/2.38$$

$$I_{Icm}=4,$$

which is shown on FIG. 4.

This demonstrates that for equal intensities at a penetration depth of one centimeter, the initial intensity, $I_o$, had to be only 5.5 for the higher voltage (42 KeV) while the $I_o$ value for 20 KeV had to be much higher at 9.5. Thus, FIG. 4 further highlights the advantage of the use of these low energy X-rays. They do not penetrate very far. The low energy portions of the spectra illustrated in FIG. 4 are almost entirely absorbed at 3 cm.

FIGS. 5–7 are generated in the same manner as FIG. 4 but for constant potential d.c. voltages of 40 KeV, 30 KeV, and 25 KeV, respectively. Information of this kind is necessary for determining suitable voltages for treating tumors of different varieties and sizes while minimizing damage to nearby tissues.

The micro-tubes are similar in principle to standard X-ray tubes except that they are much smaller and require only a small fraction of the tube current required in conventional commercial machines (i.e. microamperes vs milliamperes). The physical size of a tube can be a fraction of an inch in diameter and with a length as small as one-half of an inch, to as long as several inches. A variety of useful tube designs is possible.

Referring now to FIG. 8a, a schematic illustration of an embodiment having a filament cathode is shown, designated generally as 20. An evacuated glass tube 22 contains a stable vacuum of at least $10^{-6}$ Torr. A heated filament cathode 24 (preferably a small tungsten filament) and an anode 26 are provided which are connected to an appropriate power source (as will be discussed below). The anode 26 can be made of any one of a number of different metals typically used, but tungsten is preferred (as it is conventional commercial tubes).

Referring to FIG. 8b, a second type of X-ray tube that is suitable for micro-tube use is schematically illustrated, designated generally as 28. Tube 28 is a cold emission (or field emission) cathode tube (which has no filament). The electrons are emitted from a sharply pointed electrode 30, preferably formed of tungsten. A very high potential gradient develops between the sharply pointed tip of the electrode and the anode 32 when a high voltage is applied across the X-ray tube 28. For micro-tube use in radiation oncology, use of a cold electron emitter tube has some advantages. This type of tube is simpler to make in smaller sizes than the heated filament type.

The depth of penetration of the present X-ray microtubes can be easily controlled by varying the tube voltage. The total desired radiation exposure can be controlled by selecting an appropriate time of exposure. A great advantage of the micro-tube is that it can be placed on or very near the surface of the tumor, or within the tumor, so that radiation damage to normal tissue is minimized.

The source to tumor distance for the micro-tubes, therefore, is extremely small compared with the source to skin distance (SSD) of 20 to 50 centimeters with the X-ray units now in common use. Since the intensity of the X-ray beam varies inversely with the square of the distance from the beam source, for a given tube voltage, the same effective intensity of the X-ray beam at the site of a tumor can be produced by the micro-tube with about one one-thousandth of the current required for the proper operation of a large external tube. Therefore, the present invention operates in the low microampere range, rather than the low milliampere range required for currently used large tubes.

Micro-tubes are relatively inexpensive and may be manufactured to be re-sterilized or disposable. The exterior surface of the tube is preferably covered with a thin tough biocompatible plastic material, as will be described below, to guard against damage to handlers or patients should accidental breakage of the glass tube occur. The plastic tube cover can also have a built-in water coolant jacket to dissipate the small amount of heat generated by the tube (operating at a small fraction of a watt).

The power supply required is relatively simple and inexpensive because of the low current required (microamperes vs conventionally used milliamperes) and because of the relatively low tube voltages required (generally less than 60 kilovolts compared 60 kilovolts to one million volts for conventional equipment). Aside from the micro-tube itself, only state of the art equipment is necessary. However, one difference in detail is necessary. Conventional 60 cycle a.c. destroys the many normal nerve functions. The inventive concepts of the present invention provide for use of a frequency that would be sufficiently high so that the normal nerve functions of the body would not be affected if an inadvertent contact of the high voltage lead with body tissue did occur. The use of high frequency currents in electrosurgical cutting and coagulation machines is common and has long been known to be safe (see for example, U.S. Pat. No. 3,699,967, entitled "Electrosurgical Generator", and Chapter 3, Electrosurgery, Handbook of Biomedical Engineering, 1988, Academic Press). Furthermore, use of such high frequencies provides the ability for the patient to act as a conduit for return of the anode current back to the power supply if that anode is not directly connected to the power supply.

FIG. 8C illustrates the placement of the anode 34 and the cathode 36 on the same side of a microtube 38 to accomplish a reduced length. An internal glass tube 40 is used to support the anode 34 and to insulate the anode connecting wire 42.

The micro-tubes of the present invention may be manufactured in a variety of different ways to optimize their use. For example, in FIG. 8D(a) a glass micro-tube 42 is illustrated with a thin internal anode film 44 formed on its inner surface (preferably vacuum deposited tungsten). An axially extending filament cathode 46 is provided. Thus, when operated, a cylindrical X-ray pattern, illustrated by the arrows 48 in FIG. 8D(b), results. This design is particularly useful if the microtube is desired to be inserted near the center of the tumor.

FIGS. 8E(a) and 8E(b) illustrate a relatively thick film anode 50 deposited or otherwise formed on portions of the inside of the glass tube 52. This results in a backscattered X-ray beam which produces a hemicylindrical X-ray pattern, as illustrated by arrows 54. The X-ray pattern is established at portions of the microtube which do not have the thick film formed thereon.

In the micro-tube illustrated in FIG. 8F(a) and 8F(b) a thin anode film 56 is formed on only a portion of the micro-tube 58. This results in a hemicylindrical X-ray pattern 60.

An alternate anode design is illustrated in FIG. 8G, the micro-tube being designated as 62. In this instance, the anode 64 is a spot type of thin or thick film.

In FIGS. 8H(a) and 8H(b) a hemispherical X-ray pattern 66 results from formation of an anode film 68 near the end of the micro-tube 70.

The short micro-tubes illustrated in FIGS. 8A–8H are typically from one-fourth inch to two inches in length, preferably approx. ½". Diameters may range from ⅛" to 1", preferably ¼". As noted, these microtubes may be placed in-situ by a number of methods, including, implantation during surgery; insertion through a normal body orifice; insertion in conjunction with a fiber-optic scope through a normal body orifice; insertion in conjunction with a fiber-optic scope through a surgical incision; insertion through a trocar catheter; or insertion through a catheter contained within a surgical incision. The micro-tubes may also be placed adjacent to the body next to the skin.

Longer micro-tubes may alternately be used which may be up to several inches (i.e. 2"–8") in length. FIG. 9 illustrates a schematic of a design of such a long micro-tube 72. The lead wire 74 for the cathode 76 and the lead wire 78 for the anode 80 connect to a power supply (not shown). Long micro-tube 72 is particularly useful in the brain and is made thin, for example, in the range of ⅛" to ¼" in diameter. End 82 is enlarged and extends outside of the body, serving as a "compass" for accurately rotating the micro-tube and directing the X-rays in the desired manner. It is understood that the various features shown in the previous Figures may be implemented in the longer tubes of FIG. 9. Further, it is understood that FIGS. 8 and 9 are meant only to be schematic representations of possible micro-tube designs. Obviously, biocompatible safety shields would be utilized to enclose the tubes in actual applications.

The principles of the present invention are preferably implemented with the micro-tubes being used as part of a mechanically shielded and electrically insulated assembly. Referring now to FIG. 10, such an implementation in the form of a short liquid-cooled micro-tube assembly, designated generally as 84, is illustrated. Liquid-cooled micro-tube assembly 84 includes a filament cathode 86 supported by a filament support structure 88 within an evacuated glass tube 90. Similarly, an anode 92 is supported by another filament support structure 94 within the evacuated glass tube 90. Glass tube 90 may be formed as described in the above-discussion regarding FIGS. 8 and 9. Glass tube 90 is positioned within a liquid coolant chamber 96 which is supplied by coolant hoses 98,100. (Water would be a suitable coolant. The walls of the coolant chamber may be formed of, for example, glass or plastic). Coolant chamber 96 is, in turn, enclosed within the main housing 102 of the micro-tube assembly 84. Housing 102 is preferably formed of plastic. Filament lead wires 104,106, anode lead wire 108, and coolant hoses 98.100, extend through the main housing 102. These five elements are preferably radially spaced and separated by walls to confine any leaks to a specific portion of the assembly. Dashed lines 110 schematically illustrate these walls. Additionally, approximately water seals 112 are provided.

A metal-jacketed micro-tube assembly, designated generally as 114, is illustrated in FIG. 11. Assembly 114 includes a cathode 116 supported by a cathode support structure 118 within an evacuated glass tube 120. Similarly, an anode 122 is supported by another support structure 124 within the evacuated glass tube 120. Glass tube 120 is contained within a metal jacket 126. Tube 120 may be formed as described in the above-discussion regarding FIGS. 8 and 9. A window 128 is provided in the metal jacket 126 for directing the radiation in the desired manner. Anode and cathode cables 130,132 including lead wires are provided for attachment to an external power source (not shown).

The power supply needed for X-ray micro-tube operation is unique in that it is a low energy device that can be made easily portable and is less costly to make than those now supplied with deep therapy equipment, which require much higher levels of energy. Modern electronic designs and equipment capable of providing the currents and voltages needed for the operation of the micro-tubes are state of the art, and a variety of designs are available. Another essential feature of the invention is that the power supply circuit must contain a rapidly acting safety circuit interrupter that will immediately operate should anything happen to cause the tube current to suddenly increase to, for example, one milliampere, which is still very safe for a patient but undesirable for micro-tube operation.

Obviously, many modifications and variations of the present invention are possible in light of the above teachings. It is therefore to be understood that, within the scope of the appended claims, the invention may be practiced otherwise than as specifically described.

What is claimed and desired to be secured to Letters Patent of the United States is:

1. An apparatus for the treatment of a patient having a tumor, comprising:

an X-ray generating source insertable into the body of said patient to a location in close proximity to said tumor, said X-ray generating source comprising a substantially cylindrical glass X-ray tube having a length on the order of one-quarter to two inches and a diameter less than one inch and being operable at a voltage level in the range of approximately 10–60 KeV, thereby enhancing absorption of the generated X-rays by said tumor and minimizing the side effects of radiation therapy on the patient's normal tissue.

2. The apparatus of claim 1, wherein said X-ray generating source includes a metal-jacketed micro-tube assembly, comprising:

a) an evacuated glass tube;

b) a cathode supported within said evacuated glass tube;

c) an anode supported within said evacuated glass tube;

d) support means for supporting said cathode and said anode;

e) a metal jacket enclosing said evacuated glass tube therein, said metal jacket including a window for directing the generated radiation in the desired manner; and, f) electrical connection means for connecting said cathode and said anode to a source of electrical power.

3. The apparatus of claim 1, wherein said glass X-ray tube contains a stable vacuum of at most $10^{-6}$ Torr.

4. The apparatus of claim 3, wherein said glass X-ray tube is a cold emission cathode tube.

5. The apparatus of claim 3, wherein said glass X-ray tube includes a heated filament cathode.

6. The apparatus of claim 3, further including a power source for operating said glass X-ray tube at a frequency range of d.c. to 1,000,000 cycles per second.

7. The apparatus of claim 3, further including a power source for operating said glass X-ray tube at a frequency in the range between 70,000 and 1,000,000 cycles per second.

8. The apparatus of claim 1, wherein said glass X-ray tube has a length of approximately one inch and a diameter of approximately one-quarter inch or less.

9. The apparatus of claim 1, wherein said X-ray generating source includes a liquid-cooled micro-tube assembly, comprising:

a) an evacuated glass tube;

b) a filament cathode supported within said evacuated glass tube;

c) an anode supported within said evacuated glass tube;

d) support means for supporting said cathode and said anode;

e) a housing for supporting and enclosing said evacuated glass tube therein, a liquid coolant chamber being formed between said housing and said glass tube;

f) electrical connection means for connecting said cathode and said anode to a source of electrical power; and, g) coolant conduits for supplying coolant to said coolant chamber.

10. An X-ray micro-tube for the treatment of a patient having a tumor, comprising:

a substantially cylindrical evacuated glass X-ray tube having a length on the order of one-quarter to two inches and a diameter less than one inch and containing a stable vacuum of, at most, $10^{-6}$ Torr, said glass X-ray tube being locatable at a location in close proximity to said tumor, said X-ray tube being operable at a voltage level in the range of approximately 10–60 KeV, thereby enhancing absorption of the generated X-rays by said tumor and minimizing the side effects of radiation therapy on the patient's normal tissue.

11. The X-ray micro-tube of claim 10, wherein said glass X-ray tube operates at a frequency of between d.c. and 1,000,000 cycles per second.

12. The X-ray micro-tube of claim 11, wherein said glass X-ray tube operates at a frequency in the range between 70,000 and 1,000,000 cycles per second.

13. The X-ray micro-tube of claim 12, wherein said glass X-ray tube includes a coolant jacket positioned about its periphery.

14. The X-ray micro-tube of claim 12, further including protective shielding circumscribing said glass X-ray tube for patient protection in the event of glass breakage.

15. A method for the in-situ treatment of a patient having a tumor, comprising:

(a) providing an X-ray generating source comprising a substantially cylindrical glass X-ray tube having a length on the order of one-quarter to two inches and a diameter less than one inch and being operable at a voltage level in the range of approximately 10–60 KeV;

(b) positioning said X-ray generating source at a location in close proximity to said tumor; and, (c) applying power to said X-ray generating source in said range of approximately 10–60 KeV, thereby enhancing absorption of the generated X-rays by said tumor and minimizing the side effects of radiation therapy on the patient's normal tissue.

16. The method of claim 15 wherein said step of positioning said X-ray generating source includes inserting said source into the body of said patient to a location in close proximity to said tumor.

*17. An apparatus for the treatment of a patient having a tumor, comprising:*

*an X-ray generating source insertable into the body of said patient to a location in close proximity to said tumor, said X-ray generating source comprising a substantially cylindrical glass X-ray tube having a diameter less than one inch and being operable at a voltage level in the range of approximately 10–60 KeV, thereby enhancing absorption of the generated X-rays by said tumor and minimizing the side effects of radiation therapy on the patient's normal tissue.*

*18. An X-ray micro-tube for the treatment of a patient having a tumor, comprising:*

*a substantially cylindrical evacuated glass X-ray tube having a diameter less than one inch and containing a stable vacuum of, at most, $10^{-6}$ Torr, said glass X-ray tube being locatable at a location in close proximity to said tumor, said X-ray tube being operable at a voltage level in the range of approximately 10–60 KeV, thereby enhancing absorption of the generated X-rays by said tumor and minimizing the side effects of radiation therapy on the patient's normal tissue.*

*19. A method for the in-situ treatment of a patient having a tumor, comprising:*

*(a) providing an X-ray generating source comprising a substantially cylindrical glass X-ray tube having a diameter less than one inch and being operable at a voltage level in the range of approximately 10–60 KeV;*

*(b) positioning said X-ray generating source at a location in close proximity to said tumor; and,*

*(c) applying power to said X-ray generating source in said range of approximately 10–60 KeV, thereby enhancing absorption of the generated X-rays by said tumor and minimizing the side effects of radiation therapy on the patient's normal tissue.*

* * * * *